(12) United States Patent
Panescu et al.

(10) Patent No.: US 6,293,943 B1
(45) Date of Patent: Sep. 25, 2001

(54) TISSUE HEATING AND ABLATION SYSTEMS AND METHODS WHICH PREDICT MAXIMUM TISSUE TEMPERATURE

(75) Inventors: Dorin Panescu, Sunnyvale; Sidney D. Fleischman, Menlo Park; David K. Swanson, Mountain View, all of CA (US)

(73) Assignee: EP Technologies, Inc., Sunnyvale, CA (US)

( * ) Notice: Subject to any disclaimer, the term of this patent is extended or adjusted under 35 U.S.C. 154(b) by 0 days.

(21) Appl. No.: 09/034,977

(22) Filed: Mar. 4, 1998

Related U.S. Application Data

(63) Continuation of application No. 08/482,361, filed on Jun. 7, 1995, now abandoned.

(51) Int. Cl.$^7$ .................................................. A61B 17/39
(52) U.S. Cl. ............................... 606/41; 606/27; 606/31; 606/33; 606/34; 606/42
(58) Field of Search .................................. 606/27–34, 40, 606/41, 42, 46–49; 607/98–105; 604/20

(56) References Cited

U.S. PATENT DOCUMENTS

| | | |
|---|---|---|
| 5,122,137 | 6/1992 | Lennox . |
| 5,180,896 | 1/1993 | Gibby et al. . |
| 5,456,682 | 10/1995 | Edwards et al. . |
| 5,540,679 | 7/1996 | Fram et al. . |
| 5,623,940 | 4/1997 | Daikuzono . |

FOREIGN PATENT DOCUMENTS

| | | | |
|---|---|---|---|
| WO92/10142 | 6/1992 | (WO) . | |
| 9315664 | * 8/1993 | (WO) | ...... 606/45 |

* cited by examiner

Primary Examiner—David M. Shay
(74) Attorney, Agent, or Firm—Lyon & Lyon LLP

(57) ABSTRACT

Systems and methods heat or ablate body tissue by positioning an electrode to transmit heat or ablation energy to a tissue region. The systems and methods measure a first temperature using a temperature sensing element associated with the electrode. The systems and methods also measure a second temperature using a temperature sensing element associated with the electrode. The systems and methods process at least one of the first and second temperatures to derive a prediction of maximum temperature of the tissue region. The systems and methods generate an output that controls the transmission of the heating or ablation energy based, at least in part, upon the maximum tissue temperature prediction.

56 Claims, 11 Drawing Sheets

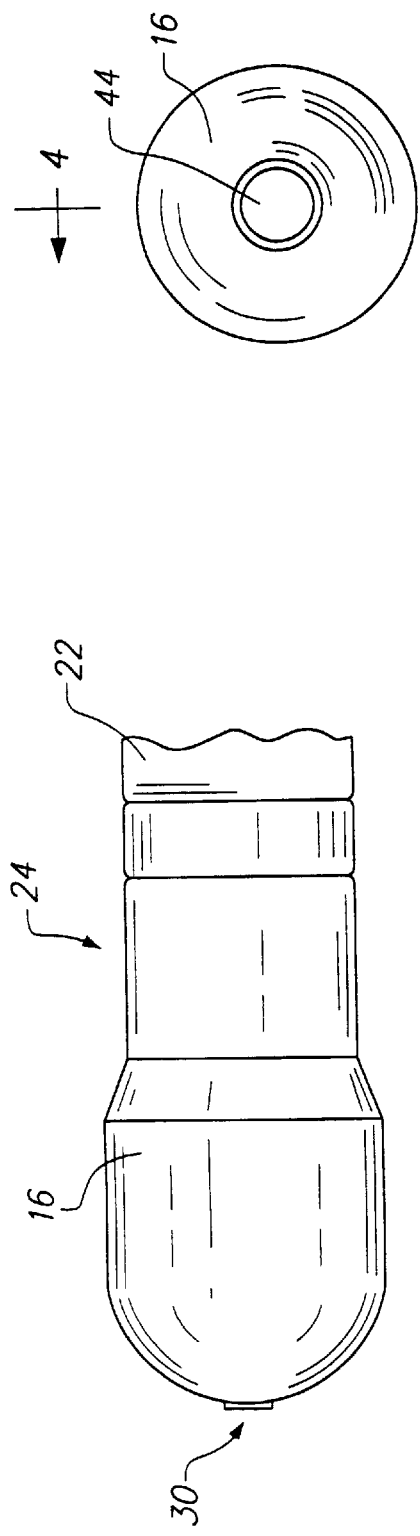
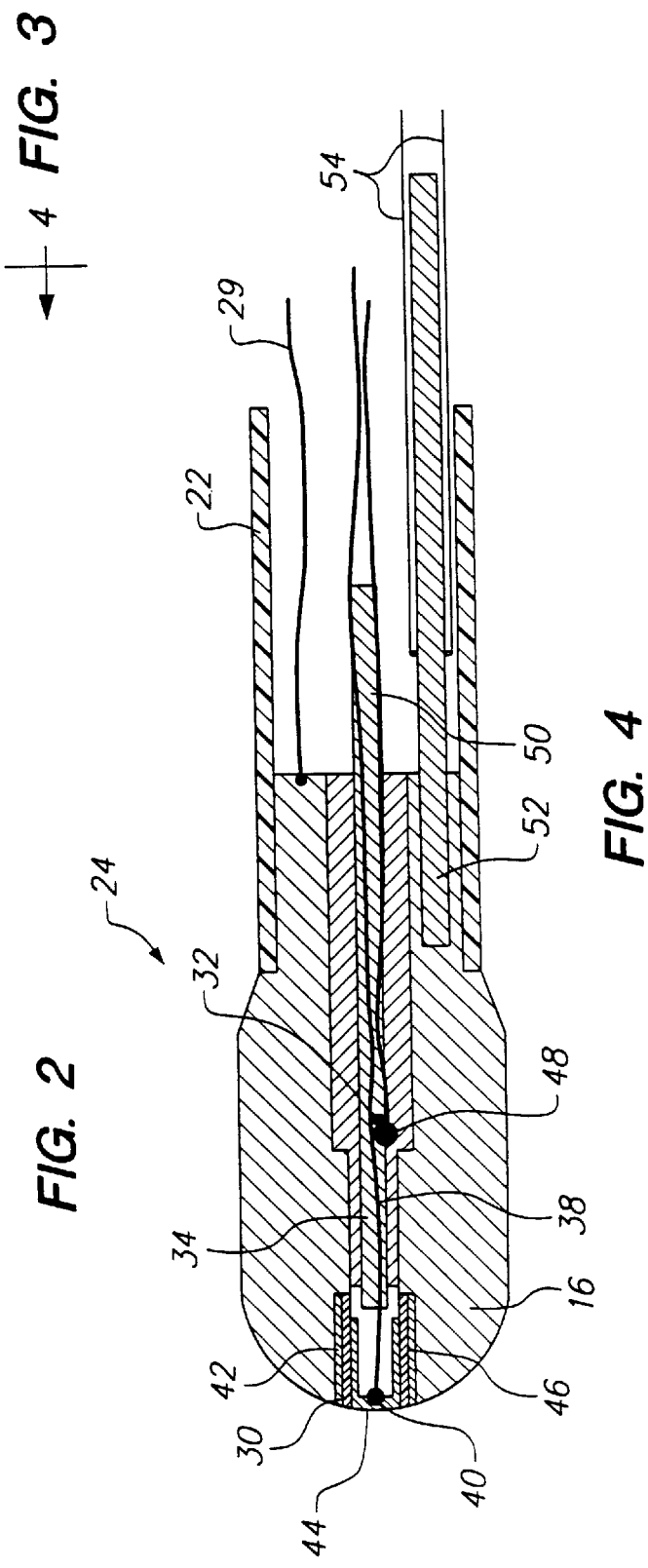

TISSUE HEATING AND ABLATION SYSTEMS AND METHODS WHICH PREDICT MAXIMUM TISSUE TEMPERATURE

This is a continuation of application Ser. No. 08/482,361, filed on Jun. 7, 1995 now abondoned.

FIELD OF THE INVENTION

In a general sense, the invention is directed to systems and methods for creating lesions in the interior regions of the human body. In a more particular sense, the invention is directed to systems and methods for ablating heart tissue for treating cardiac conditions.

BACKGROUND OF THE INVENTION

Physicians frequently make use of catheters today in medical procedures to gain access into interior regions of the body. In some procedures, the catheter carries an energy transmitting element on its distal tip to ablate body tissues.

In such procedures, the physician must establish stable and uniform contact between the energy transmitting element and the tissue to be ablated. Upon establishing contact, the physician must then carefully apply ablating energy to the element for transmission to the tissue.

The need for precise control over the transmission of ablation energy is especially critical during catheter-based procedures for ablating heart tissue. These procedures, called electrophysiology therapy, are becoming increasingly more widespread for treating cardiac rhythm disturbances, called arrhythmias. Cardiac ablation procedures typically use radio frequency (RF) energy to form a lesion in heart tissue.

The principal objective of the invention is to provide systems and methods for monitoring and reliably controlling the application of energy to ablate body tissue, thereby providing therapeutic results in a consistent and predictable fashion.

SUMMARY OF THE INVENTION

The invention provides systems and methods that provide reliable control over tissue heating and ablation procedures using temperature sensing.

The systems and methods heat or ablate body tissue by positioning an electrode to transmit heat or ablation energy to a tissue region. The systems and methods measure a first temperature using a temperature sensing. element associated with the electrode. The systems and methods also measure a second temperature using a temperature sensing element associated with the electrode. The systems and methods process at least one of the first and second temperatures to derive a prediction of maximum temperature of the tissue region.

In a preferred embodiment, the systems and methods generate an output that controls the transmission of the heating or ablation energy based, at least in part, upon the maximum tissue temperature prediction.

Other features and advantages of the inventions are set forth in the following Description and Drawings, as well as in the appended claims.

BRIEF DESCRIPTION OF THE DRAWINGS

FIGS. 2, 3 and 4 are, respectively, an elevated side view, an end view, and a side section view (taken along line 4—4 in FIG. 3) of the electrode associated with the system shown in FIG. 1, the electrode having two temperature sensing elements;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
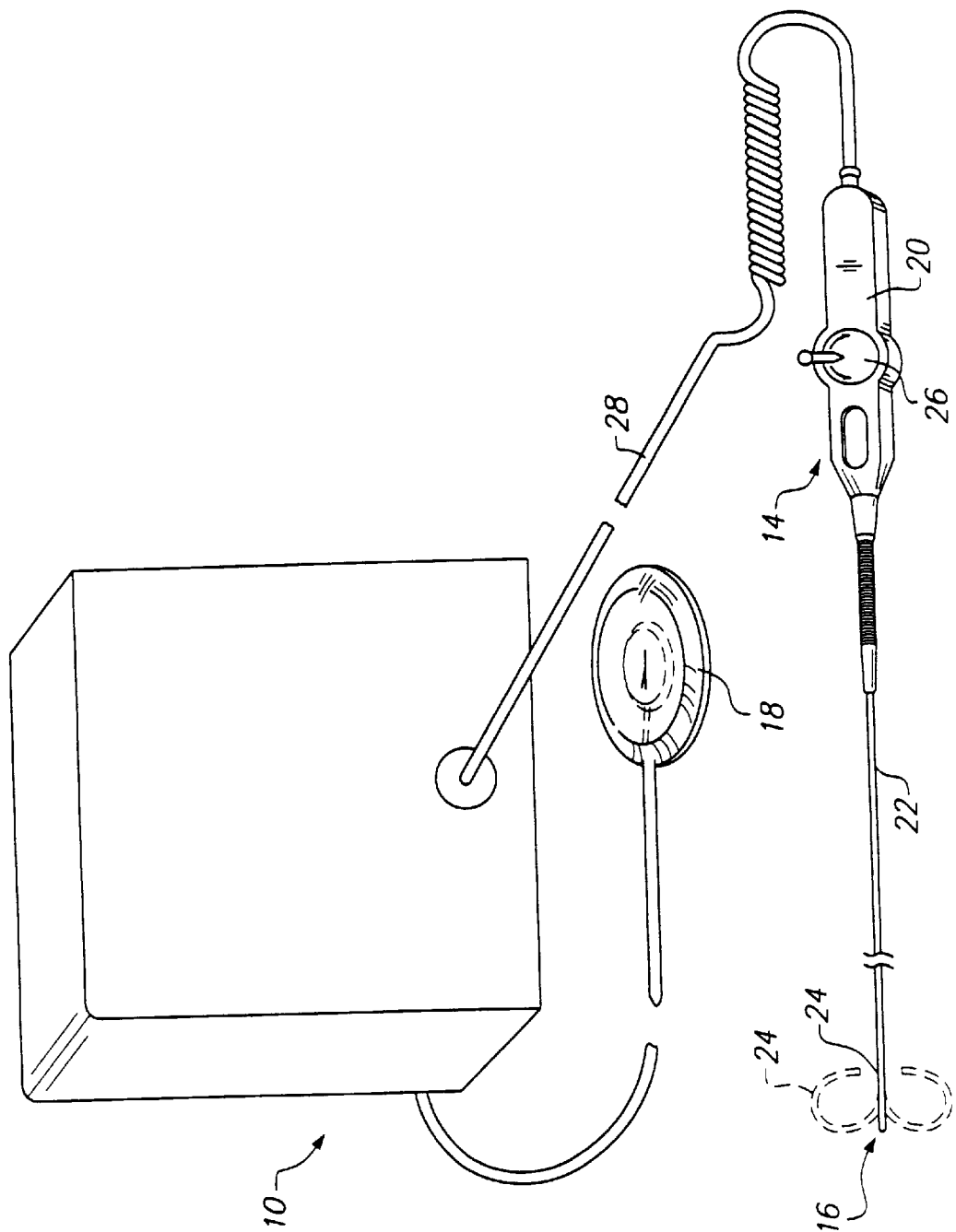
FIG. 1 is a perspective view of a system for ablating tissue that comprises an energy emitting electrode and associated energy generator.

FIG. 1 shows a system 10 for ablating human tissue that embodies the features of the invention.

In the illustrated and preferred embodiment, the system 10 includes a generator 12 that delivers radio frequency energy to ablate tissue. Of course, other types of energy can be generated for tissue ablating purposes.

The system 10 also includes a steerable catheter 14 carrying a radio frequency transmitting ablation electrode 16. In the illustrated embodiment, the ablation electrode 16 is made of platinum.

In the illustrated embodiment, the system 10 operates in a unipolar mode. In this arrangement, the system 10 includes a skin patch electrode that serves as an indifferent second electrode 18. In use, the indifferent electrode 18 attaches to the patient's back or other exterior skin area.

Alternatively, the system 10 can be operated in a bipolar mode. In this mode, the catheter 14 carries both electrodes.

The system 10 can be used in many different environments. This specification describes the system 10 when used to provide cardiac ablation therapy.

When used for this purpose, a physician steers the catheter 14 through a main vein or artery (typically the femoral vein or artery) into the interior region of the heart that is to be treated. The physician then further manipulates the catheter 14 to place the electrode 16 into contact with the tissue within the heart that is targeted for ablation. The user directs radio frequency energy from the generator 12 into the electrode 16 to ablate and form a lesion on the contacted tissue.

In the embodiment shown in FIG. 1, the catheter 14 includes a handle 20, a catheter body 22, and a distal tip 24, which carries the electrode 16.

The handle 20 encloses a steering mechanism 26 for the catheter tip 24. A cable 28 extending from the rear of the handle 20 to connect the catheter 14 to the generator 12 for conveying radio frequency energy to the ablation electrode 16 via a signal wire 29 (see FIG. 4).

Left and right steering wires 54 (see FIG. 4) are connected to a steering spring 52 at the tip of the catheter body 22. The steering wires extend through the catheter body 22 to interconnect the steering mechanism 26 in the handle 20 (see FIG. 1). Rotating the steering mechanism 26 to the left pulls on the left steering wire, causing the spring 52 and tip 24 to bend to the left. In the same way, rotating the steering mechanism 26 to the right causes the spring 52 and tip 24 to bend to the right. In this way, the physician steers the ablation electrode 16 into contact with the tissue to be ablated.

Further details of this and other types of steering mechanisms for the ablating element 10 are shown in Lunquist and Thompson U.S. Pat. No. 5,254,088, which is incorporated into this Specification by reference.

I. Multiple Temperature sensing

As FIGS. 2 to 4 show, the ablation electrode 16 carries two temperature sensing elements 30 and 32. As will be described in greater detail later, the power that the generator 12 applies to the electrode 16 is set, at least in part, by the temperature conditions sensed by the elements 30 and 32.

As best shown FIGS. 3 and 4, the ablation electrode 16 includes an interior well 34 extending through its center. The two temperature sensing elements 30 and 32 occupy this well 34.

In the illustrated embodiment, the first temperature sensing element 30 is carried within a cap 42 at the distal extremity of the well 34. In use, the sensing element 30 is intended to make thermal conductive contact with tissue, to thereby sense tissue temperature.

Lead wires 38 extend from the sensing element 30 through the catheter body 22 into the catheter handle 20. There, the lead wires 38 electrically couple to the cable 28 for connection to the generator 12. The lead wires 38 transmit the tissue temperature signals from the temperature sensing element 30 to the generator 12.

In the illustrated and preferred embodiment, the sensing element 30 comprises a conventional small bead thermistor 40. For example, a 0.55 mm bead thermistor commercially available from Thermometrics (Edison, N.J.), Part Number AB6B2-GC16KA143E/37° C-A can be used.

The sensing element 30 and lead wires 38 are electrically insulated from the surrounding ablation electrode 16. For this purpose, electrically insulating potting compound, such as heavy isomid, cyanoacrylate adhesive, silicon rubber RTV adhesive, polyurethane, epoxy, or the like, encapsulates the thermistor bead 40 in conventional fashion. The lead wires 38 are likewise enclosed in electrically insulating sheaths made from, for example, polyimide material, although other conventional electrical insulating materials also can be used.

The cap 42 is made from a thermal conducting material having a high thermal conductivity that is at least 1.0 watt (W) per meter (m) Kelvin (K), or 1.0 W/m K. Metallic materials like stainless steel, gold, silver alloy, platinum, copper, nickel, titanium, aluminum, and compositions containing stainless steel, gold, silver, platinum, copper, nickel, titanium, and aluminum possess this degree of thermal conductivity. The encapsulated thermistor bead 40 is preferably potted within the cap 42 using an electrically insulating epoxy having an enhanced thermal conductivity that is at least 1.0 W/m K. The inclusion of a metallic paste (for example, containing aluminum oxide) in a standard epoxy material will provide this enhanced thermal conductivity.

The cap 42 is fitted within the well 34 of the electrode 16 with its distal end 44 making thermal conductive contact with the tissue. The high thermal conductivity of the cap material assures that the cap 42 will quickly reach an equilibrium temperature close to that of the tissue it contacts.

In the illustrated and preferred embodiment, a thermal and electrically insulating barrier 46 forms an interface between the interior wall of the well 34 and the side of the cap 42 that occupies it. In a preferred embodiment, the barrier 46 comprises polyamide adhered about the sidewall of the cap 42 using FMD-14 to serve as an electrical insulator. The barrier 46 also comprises polyester shrink tubing secured by heat shrinking about the polyamide to serve as a thermal insulator. In the illustrated and preferred embodiment, the thermistor-containing cap 42 and associated barrier 46 are affixed and potted within the electrode well using cyanoacrylate FMD-13 (Loctite Corporation, Newington, Conn.).

The thermal conducting cap 42 creates an isothermal condition about the sensing element 30 close to the actual temperature of the tissue it contacts. Furthermore, the cap 42, being substantially isolated from thermal conductive contact with the electrode 16, retains this isothermal condition about sensing element 30, preventing its dissipation by the thermal mass of the electrode 16. Further details of the use and construction of the thermal conducting cap 42 are found in copending U.S. patent application Ser. No. 08/432, 321, filed May 1, 1995, and entitled "Systems and Apparatus for Sensing Temperature in Body Tissue", which is incorporated herein by reference.

The second temperature sensing element 32 carried within the well 34 is connected by soldering or by thermal conductive adhesive in direct thermal conductive contact with the thermal mass of the electrode 16. While transmitting radio-frequency energy to heat surrounding tissue, the electrode 16 is heated by thermal conduction from the heated tissue. In use, the second sensing element 32 is intended to sense the temperature of the electrode 16 due to conductive heat transfer.

In the illustrated and preferred embodiment, the sensing element 32 also comprises a conventional small bead thermistor 48, as already described in connection with the sensing element 30. Also, like the sensing element 30, the sensing element 32 is electrically insulated from the electrode 16 by encapsulation in an electrically insulating potting compound, as also already described.

The thermistor 48 also has associated lead wires 50, which extend through the catheter body 22 and handle 20 to the cable 28. The cable 28 transmits the electrode temperature signals from the temperature sensing element 32 to the generator 12.

It should be appreciated that the first temperature sensing element 30 need not be positioned in thermal conductive contact with tissue. The first element 30 can, like the second element 32, be positioned in thermal conductive contact with the electrode 16. It is also not necessary that one or both sensing elements 30 and 32 be in direct thermal conductive contact with the electrode 16. The invention requires only that the two temperature sensing elements 30 and 32 be positioned relative to the electrode 16 in a spaced apart condition to measure a meaningful spatial temperature gradient at the tissue-electrode interface.

It should also be appreciated that the electrode 16 need not be in direct contact with tissue. Laser and microwave transmitting electrodes can carry the spaced apart temperature sensing elements 30 and 32 and perform tissue ablation according to invention without contacting the ablated tissue.

The apparatus and methods that embody the features of the invention are well suited for use in the field of cardiac ablation, which the preferred embodiments exemplify. Still, the invention is applicable for use in tissue heating applications, as well. For example, the various aspects of the invention have application in procedures for ablating or heating tissue in the prostrate, brain, gall bladder, uterus, and other regions of the body, using systems that are not necessarily catheter-based.

It should be appreciated that other types of temperature sensing elements can also be used. For example, a thermocouple could be used as the temperature sensing element. In a preferred implementation, the thermocouples are constructed by either spot welding or by laser stripping and welding the different metals together to form the thermocouple junction. When a thermocouple serves as the temperature sensing element, a reference thermocouple must be used. The reference thermocouple may be placed in the handle 20, generator 12, or exposed to the blood pool in the manner disclosed in copending U.S. patent application Ser, No. 08/286,937, filed Aug. 8, 1994, and entitled "Systems and Methods for Sensing Temperature Within the Body."

Electrical insulation is also required when thermocouples are used as the temperature sensors. For example, the thermocouple junction can be placed in a thermally conducting epoxy inside a polyester sleeve. In a preferred implementation, the thermocouple junction is placed in UV modified acrylic adhesive 330(Loctite Corporation, Newington, Conn.) within a shrink polyester sleeve, which is then shrunk to fit tightly about the thermocouple junction and wires. To reduce electrical interference, the thermocouple wires are also preferably electrically shielded and twisted together.

II. The RF Generator

Figure 5:
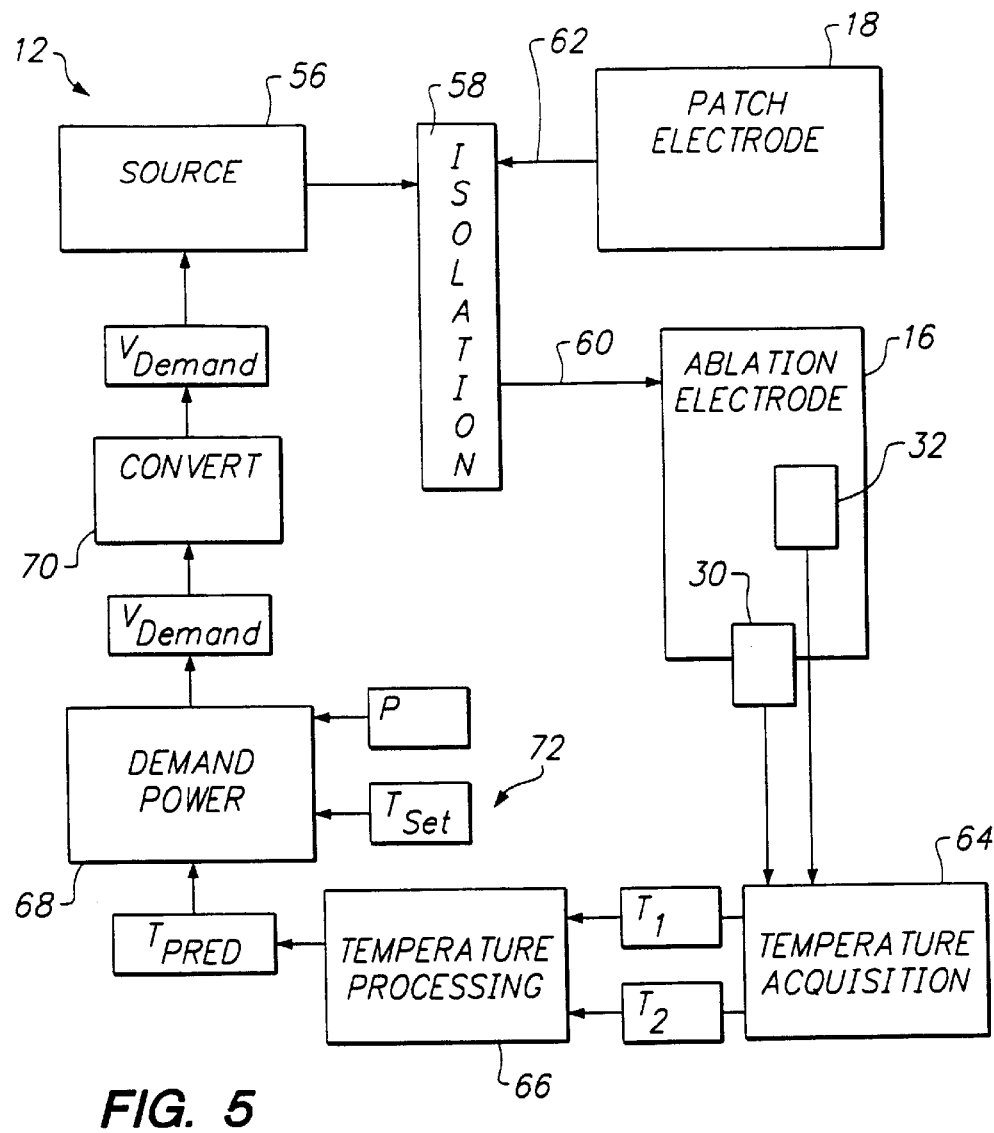
FIG. 5 is a schematic view of the generator for supplying energy to the electrode in the system shown in FIG. 1, the generator using a specialized modified PID control technique to maintain a desired set temperature by altering power in response to a prediction of maximum tissue temperature.

As FIG. 5 shows, the generator 12 includes a radio frequency power source 56 connected through a main isolation transformer 58 to outlet and return lines 60 and 62. Outlet line 60 leads to the ablation electrode 16. Return line 62 leads from the indifferent electrode 18.

In the illustrated embodiment, when used for cardiac ablation, the power source 56 is typically conditioned to deliver up to 150 watts of power at a radio frequency of 500 kHz.

The generator 12 further includes a temperature acquisition system 64, a temperature processing element 66, a demand power processor 68, and a converter 70. These components comprise a feedback loop, which couples the two temperature sensing elements 30 and 32 to the source 56 for making applied radio-frequency energy responsive to sensed temperature conditions.

The temperature acquisition system 64 is coupled to the two temperature sensing elements 30 and 32. The system 64 continuously samples at prescribed time periods, t, the analog signals generated by the sensing elements 30 and 32 based upon sensed temperature conditions. The system 64 converts the separate analog signals of the sensing elements 30 and 32 into individual, proportional digital signals, respectively tissue temperature $T_1(t)$ and electrode temperature $T_2(t)$.

The temperature processing element 66 is coupled to the temperature acquisition system 64 to receive as input the digital signals tissue temperature $T_1(t)$ and electrode temperature $T_2(t)$. The processing element 66 applies prescribed criteria to these actual temperature signals to derive, for the sampled time interval, a prediction of the hottest tissue temperature present in the tissue region in the vicinity of the electrode 16, $T_{pred}(t)$ The demand power processor 68 periodically compares $T_{pred}(t)$ to a set temperature value $T_{set}$. The set temperature value $T_{SET}$ can be inputted by the physician through an interface 72. The set temperature value $T_{SET}$ represents the maximum tissue temperature the physician wants to maintain at the ablation site. The value $T_{SET}$ can be established in other ways. For example, the value $T_{SET}$ can vary over time to define a set temperature curve.

The set temperature value $T_{SET}$ selected depends upon the desired therapeutic characteristics of the lesion. Typical therapeutic lesion characteristics are the surface area of the tissue that is ablated and depth of the ablation. Typically, the set temperature $T_{SET}$ is in the range of 50 to 90 degrees C.

Based upon this comparison, and preferably taking into account the magnitude of the instantaneous power P(t) supplied to the ablating electrode 16, the processor 68 derives the demand power output $P_{DEMAND}(t)$. The demand power output $P_{DEMAND}(t)$ represents the magnitude of the radio frequency power that should be supplied to the ablating electrode 16 to establish or maintain the desired local temperature condition TSET at the ablating electrode 16. By taking into account the magnitude of the instantaneous power P(t), the processor 68 assures that a prescribed maximum power level $P_{MAX}$ is not exceeded.

The manner in which the processor 68 derives $P_{DEMAD}(t)$ can vary. For example, it can employ proportional control principles, proportional integral derivative (PID) control principles, adaptive control, neural network, and fuzzy logic control principles.

EXAMPLE 1

The following Example 1 shows an exemplary core PID control algorithm that the processor 68 can employ for controlling power based upon predicted tissue temperature.

In this example, $K_p$, $K_d$, and $K_i$ are, respectively, the proportional, derivative, and integral coefficients of the PID algorithm used for controlling power based on predicted tissue temperature. The same algorithm was used to control actual tissue temperature in the comparisons presented in FIGS. 7 A/B and 8 A/B, to be discussed in greater detail later.

In this algorithm, the power at time t+1 is controlled based upon the difference between the temperature and the set temperature at times t, t−1, and t−2 (expressed in Kelvin or degrees Celsius), as follows:

power (t+1)=7W*{$K_p$*(T(t)−$T_{SET}$)+$K_d$*[(T(t)−$T_{SET}$)−(T(t−1)−$T_{SET}$)]+$K_i$*[(T(t)−$T_{SET}$)+(T(t−1)−$T_{SET}$)+T(t−2)−$T_{SET}$)]}

Data collected from the finite element analysis presented below (in Section III(A)) demonstrates that the following coefficients can be used:

$K_p$=0.04
$K_i$=0.005
$K_d$=0.008

The multiplier "7 W" appearing in the above algorithm reflects that the finite element analysis, from which the coefficients were derived, computed the power-to-temperature transfer function of the modeled system at a 7 watt (W) level.

The foregoing example sets forth the core of the control algorithm for deriving p(I) (i.e., $P_{Demand}$, based upon a fixed value of $T_{SET}$. The algorithm can include other auxiliary features.

For example, $T_{SET}$ can be expressed as a function with respect to time, which can be linear, or nonlinear, or both.

As another example, $P_{Demand}$ derived by the algorithm can be compared to a maximum power condition. Should $P_{Demand}$ exceed the maximum power condition, the controller 68 blocks passage of $P_{Demand}$ and instead commands a preestablished low power condition until $P_{Demand}$ becomes less than the maximum power.

Other representative implementations are disclosed in copending patent application Ser. No. 08/266,934, filed Jun. 27, 1994, and entitled "Tissue Heating and Ablation Systems and Methods Using Predicted Temperature for Monitoring and Control."

The converter 70 derives a command voltage signal $V_{DEMAND}(t)$ based upon the demand power output $P_{DEMAND}$ (t) The command voltage signal $V_{DEMAND}(t)$ adjusts the amplitude of the voltage $V_{(t)}$ supplied to the source 56 to thereby adjust $P_{(t)}$, Alternatively, the converter 70 could derive a command current signal $I_{DEMAND}(t)$ based upon the demand power output $P_{DEMAND}$ (t) to adjust the amplitude of the current supplied to the source 56, achieving the same results.

The manner in which the converter 70 generates $V_{DEMAND}(t)$ to adjust P(t) can vary. For example, the converter 70 can employ proportional control principles, proportional integral derivative (PID) control principles, neural network, fuzzy logic, and adaptive control principles. Representative implementations are disclosed in copending Patent Application Serial No. 08/266,934, filed Jun. 27, 1994, and entitled "Tissue Heating and Ablation Systems and Methods Using Predicted Temperature for Monitoring and Control".

III. Derivin $T_{PRED}(t)$

A. Prediction Based Upon An Analytical Function

The quantity $T_{PRED}$ can be expressed in terms of an analytical function $f(T_1, T_2)$, which sets forth, for a given electrode geometry, the variation of hottest tissue temperature $T_{MAX}$ with sensed tissue temperature $T_1$ and sensed electrode temperature $T_2$. The function is determined for a given electrode geometry by tabulating in vitro or in vivo results, measuring $T_1$, $T_2$, and $T_{MAX}$, and generating finite element models for the same electrode geometries to estimate $T_{PRED}$, until the modeled $T_{PRED}\approx$measured $T_{MAX}$.

EXAMPLE 2

Determining an Analytical $T_{PRED}$ Function

A three-dimensional finite element model is created for an 8F diameter/5 mm long radio frequency ablation electrode placed in a blood pool in contact with an approximately 4 cm thick rectangular slice of cardiac tissue at tissue-electrode angles of 0° and 90°. The electrode has two temperature sensing elements, as shown in FIGS. 2 to 4, one electrically and thermally isolated at the tip for sensing tissue temperature and the other electrically isolated but in thermal conductive contact with the electrode for sensing electrode temperature. The tip of the electrode extends about 1.3 mm into the tissue. The overall volume is a parallelepiped 8 cm long, 4 cm wide, and 4 cm thick. The model has 8144 nodes, using hexahedral elements and a nonuniform mesh.

The current density boundary conditions are set at the electrode, so that the maximum tissue temperature ($T_{MAX}$) reaches about 95° C. after 120 seconds.

COSMOS is used on a Hewlett Packard workstation to perform the electrical-thermal, transient analyses for 120 seconds. The analyses estimate the function that defines the relationship between $T_1$, $T_2$, and the predicted maximal tissue temperature.

Figure 6:
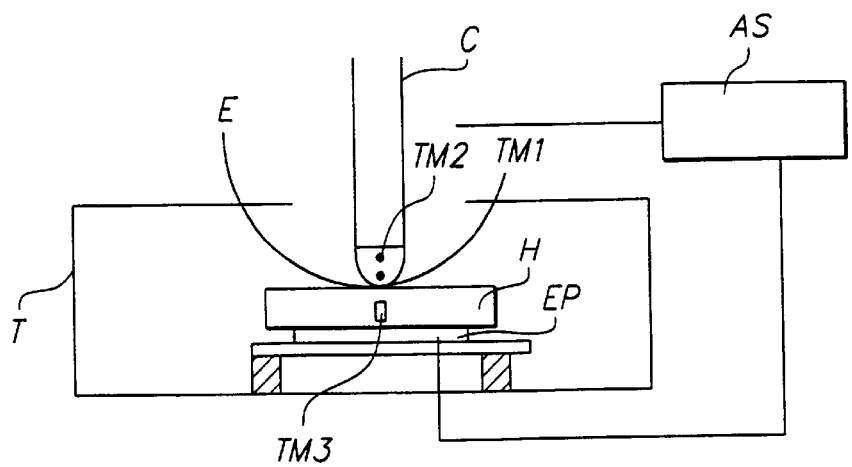
FIG. 6 is a schematic view of a device used to experimentally determine the relationship between maximum tissue temperature and the temperatures sensed by two sensing elements carried by an electrode.

The model results are corroborated with experimental data acquired using the apparatus shown in FIG. 6. A 4 cm thick slice of bovine heart H is fixed in good contact with a 144 $cm^2$ patch electrode EP inside a tank T filled with saline at 37° C. An ablation catheter C carrying an 8F diameter/5 mm long electrode E is placed in contact with the tissue surface H at an angle of 0° and 90°. A 0.55 mm bead thermistor TM1 is placed at the electrode tip (to sense $T_1$), another 0.55 mm bead thermistor TM2 is placed within the electrode (to sense $T_2$), and a third thermistor TM3 is placed in the cardiac tissue H about 0.5 mm beneath the electrode tip, which corresponds to the hottest tissue temperature region predicted by the finite element simulations. The thermistor readings are acquired at a sampling rate of 20 ms by LabView running on a Power Mac. A 500 kHz sinusoidal signal is applied between the ablation and indifferent electrodes using a 150 W RF ablation system AS. The delivered RF power (P) is kept constant at 7 W.

Using the above-described methodology, the following function was determined to yield good results for the 8F/5 mm electrode:

$$T_{pred}(t) = 4.03 * T_1(t) - 2.97 * T_2(t)$$

The above-described methodology can be used to derive the function for other electrode geometries, as well.

Figure 7A:
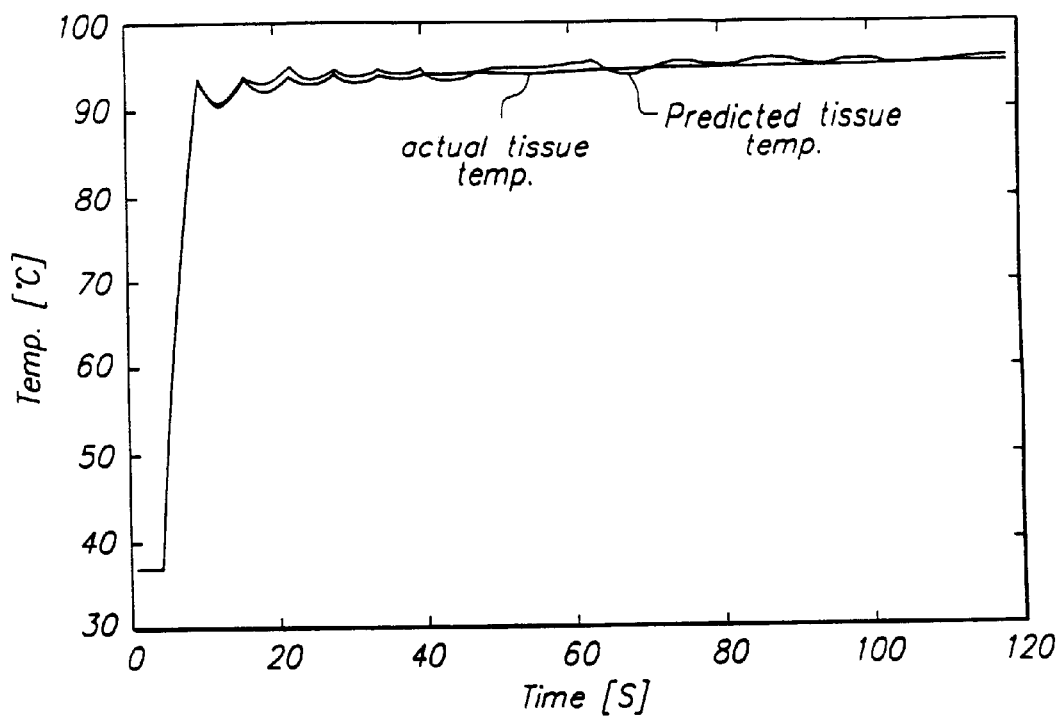
FIG. 7A is a graph presenting a comparison, for an electrode-tissue angle of 90°, of the temperature variations with time when the actual highest tissue temperature controlled the application of radio frequency energy compared when a predicted maximum tissue temperature, calculated according to the invention, was used as the control input.
Figure 7B:
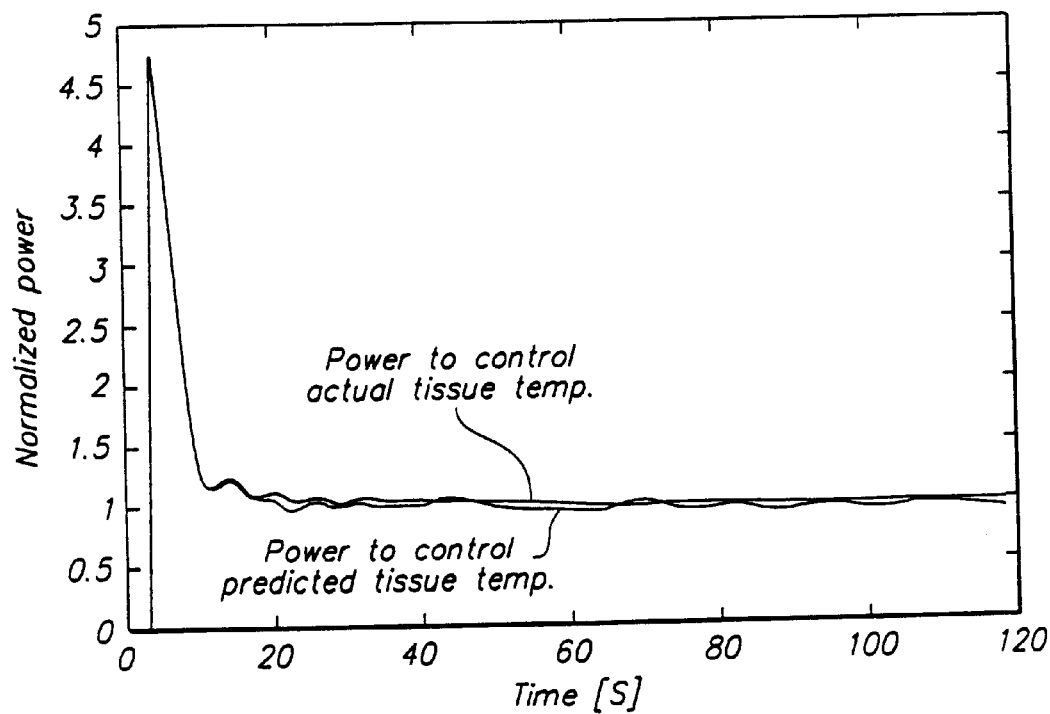
FIG. 7B is a graph presenting a comparison of applied power versus time under the same conditions set forth in FIG. 7A.
Figure 8A:
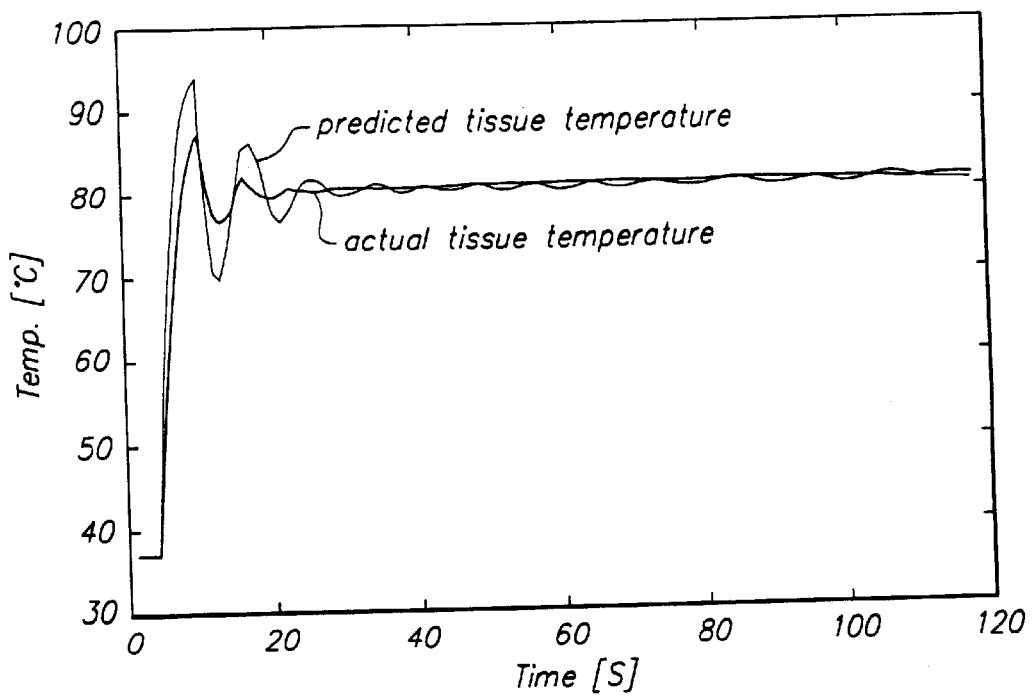
FIG. 8A is a graph presenting a comparison, for an electrode-tissue angle of 0°, of the temperature variations with time when the actual highest tissue temperature controlled the application of radio frequency energy compared when a predicted maximum tissue temperature, calculated according to the invention, was used as the control input.
Figure 8B:
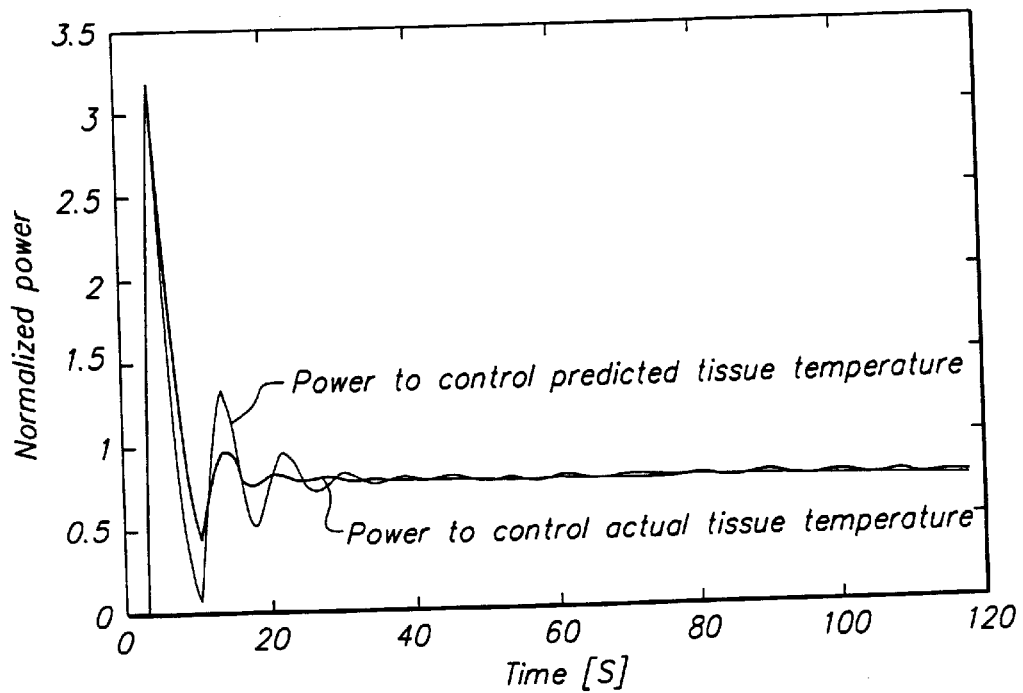
FIG. 8B is a graph presenting a comparison of applied power versus time under the same conditions set forth in FIG. 8A.

The behavior of the function for an 8F/5 mm electrode is acceptable at both tissue-electrode angles of 0° and 90°. FIG. 7A presents a comparison, for an electrode-tissue angle of 90°, of the temperature variations with time when the actual highest tissue temperature controlled the application of radio frequency energy compared when $T_{pred}$, calculated according to the above function, was used as the control input, using the PID control algorithm like that disclosed above. FIG. 7B presents a comparison of applied power versus time under the same conditions. FIGS. 8A and 8B present similar comparisons for a tissue-electrode angle of 0°. Both comparisons show that any overshoot and settling time will, in time, converge to zero.

Since the data reflected in FIGS. 7B and 8B are based upon a finite element analysis conducted at 7 W, the numbers on the y-axis shown in FIGS. 7B and 8B should be multiplied by 7 W to obtain the true power levels.

FIGS. 7B and 8B also show that keeping the temperature at a fixed set value requires a continuous, slow ramping down of applied power. This is because the temperature of heart tissue, when heated at a constant applied power, does not actually reach a steady state below 100° C. Instead, maximum tissue temperature is observed to continuously increase at a slow rate until it reaches 100° C., at which time micro-explosions occur. This rate is defined by the expression:

$$\frac{\partial T}{\partial t} = \frac{1}{\rho \cdot c} j \cdot E > 0$$

where:

T is tissue temperature.

t is time.

$\partial T/\partial t$ is the first temporal derivative of the temperature.

$\rho$ is tissue density.

c is heat capacity of the tissue.

j is current density.

E is electric field intensity.

As FIGS. 7B and 8B show, there is, for a given electrode geometry and electrode-tissue angle, a determinable rate at which power decreases to maintain a predicted maximum tissue temperature. In FIG. 7B, the rate is 0.008 W/sec for an 8F/5 mm electrode and a 90° tissue-electrode angle. In FIG. 8B, the rate is 0.003 W/sec for an 8F/5 mm electrode and a 0° tissue-electrode angle. The temperature processor 66 can ascertain this power-down rate upon deriving $T_{PRED}$ (t) using preestablished look-up tables. The processor 66 can generate the power-down rate as output to the demand power processor 68, instead of $T_{PRED}$(t). The processor 68 would control predicted tissue temperature by ramping down the power transmitted by the electrode based upon the power-down rate.

B. Prediction Based Upon Neural Networks

Figure 9:
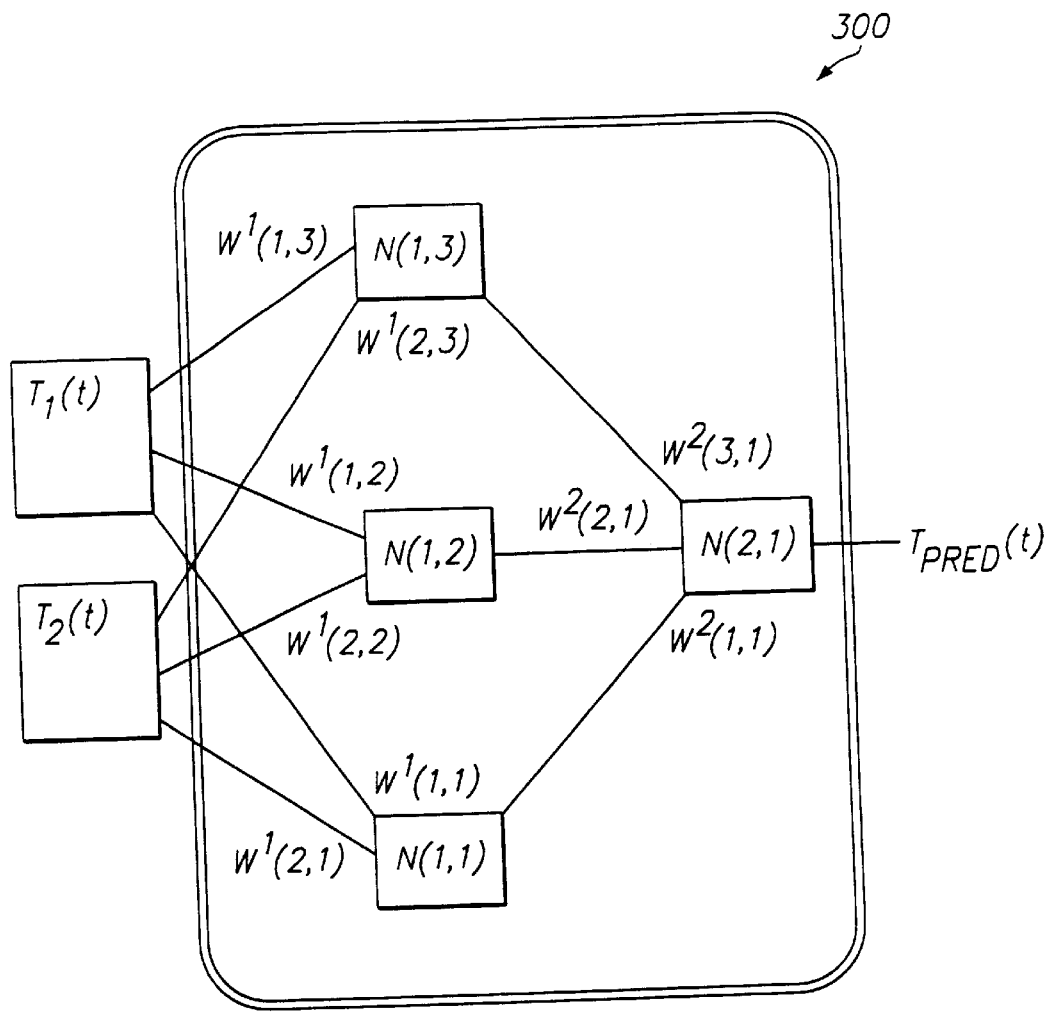
FIG. 9 is a schematic view of the implementation of a neural network predictor to predict maximum tissue temperature.

The dependence of maximum tissue temperature on $T_1$ and $T_2$ can also be approximated using neural networks. FIG. 9 shows an implementation of a neural network predictor 300, which receives as input the temperatures $T_1(t)$ and $T_2(t)$ sensed at the electrode. The predictor 300 outputs a predicted temperature of the hottest tissue region $T_{PRED}(t)$.

The predictor 300 uses a two-layer neural network, although more or less hidden layers could be used. As shown in FIG. 9, the predictor 300 includes first and second hidden layers and four neurons, designated N(L,X), where L identifies the layer 1 or 2 and X identifies a neuron on that layer. The first layer (L=1) has three neurons (X=1 to 3), as follows N(1,1); N(1,2); and N(1,3). The second layer (L=2) comprising one output neuron (X=1), designated N(2,1).

Temperature readings from the multiple sensing elements are weighed and inputted to each neuron N(1,1); N(1,2); and N(1,3) of the first layer. FIG. 9 represents the weights as $W^L(k,N)$, where L=1; k is the input sensor order; and N is the input neuron number 1, 2, or 3 of the first layer.

The output neuron N(2,1) of the second layer receives as inputs the weighted outputs of the neurons N(1,1); N(1,2); and N(1,3). FIG. 9 represents the output weights as $W^L(O, X)$, where L=2; O is the output of neuron 1, 2, or 3 of the first layer; and X is the input neuron number of the second layer. Based upon these weighted inputs, the output neuron N(2,1) predicts $T_{PRED}(t)$. Alternatively, a sequence of past reading samples from each sensor could be used as input. By doing this, a history term would contribute to the prediction of the hottest tissue temperature.

The predictor 300 must be trained on a known set of data containing the temperature of the sensing elements $T_1$ and $T_2$ and the temperature of the hottest region, which have been previously acquired experimentally in the manner set forth in the foregoing example. For example, using a back-propagation model, the predictor 300 can be trained to predict the known hottest temperature of the data set with the least mean square error. Once the training phase is completed, the predictor 300 can be used to predict $T_{PRED}(t)$.

EXAMPLE 3

Tissue Temperature Prediction Using Neural Networks

Figure 10:
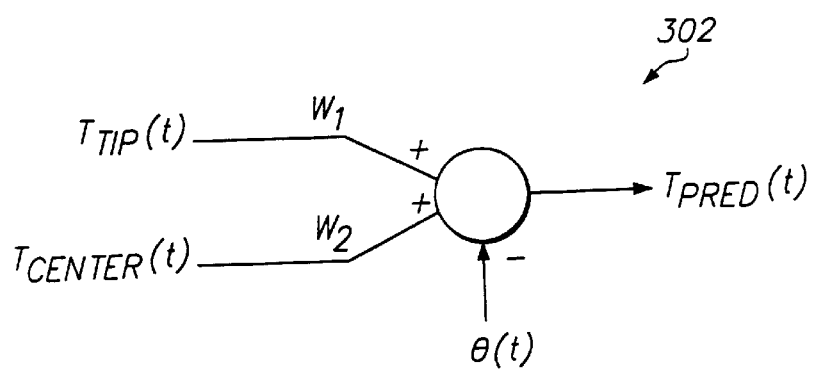
FIG. 10 is a representative single-perception network that can be used to predict maximum tissue temperature according to the invention.

FIG. 10 shows a single perceptron network 302 with inputs $T_{TIP}(t)$ and $T_{CENTER}(t)$ corresponding with temperatures sensed by sensing element 30 and sensing element 32, respectively. The output is $T_{PRED}(t)$. Weights $w_1$ and $w_2$ and bias $\theta(t)$ are used.

This network 302 computes $T_{PRED}(t)$ as follows:

$$u(t) = w_1 * (T_{TIP}(t) - T_{TIP}(0)) + w_2 * (T_{CENTER}(t) - T_{CEMTET}(0)) - \theta$$

$$y(t) = 2/(1 + \exp(-0.002 * u(t))) - 1$$

$$T_{PRED}(t) = 150 * y(t) + 37$$

The relationship between y(t) and u(t) is an activation function, which, in the above network 302, is a sigmoidal function. The factor "150" in the last equation is required because of the chosen activation function. The term "37" reflects the temperature of the tissue before ablation, i.e., body temperature. The coefficients are derived based on the experimental data presented above in Section III(A) with the apparatus shown in FIG. 6

The weights $w_1$ and $w_2$ and the bias term $\theta(t)$ were set based upon training on four experimental sets of data. During the training sessions, the weights and bias terms were updated using the back-propagation algorithm described in S. Haykin, "Neural Networks," IEEE Press (New York), 1994. The final values were computed by averaging the results in the four training sessions.

Figure 11:
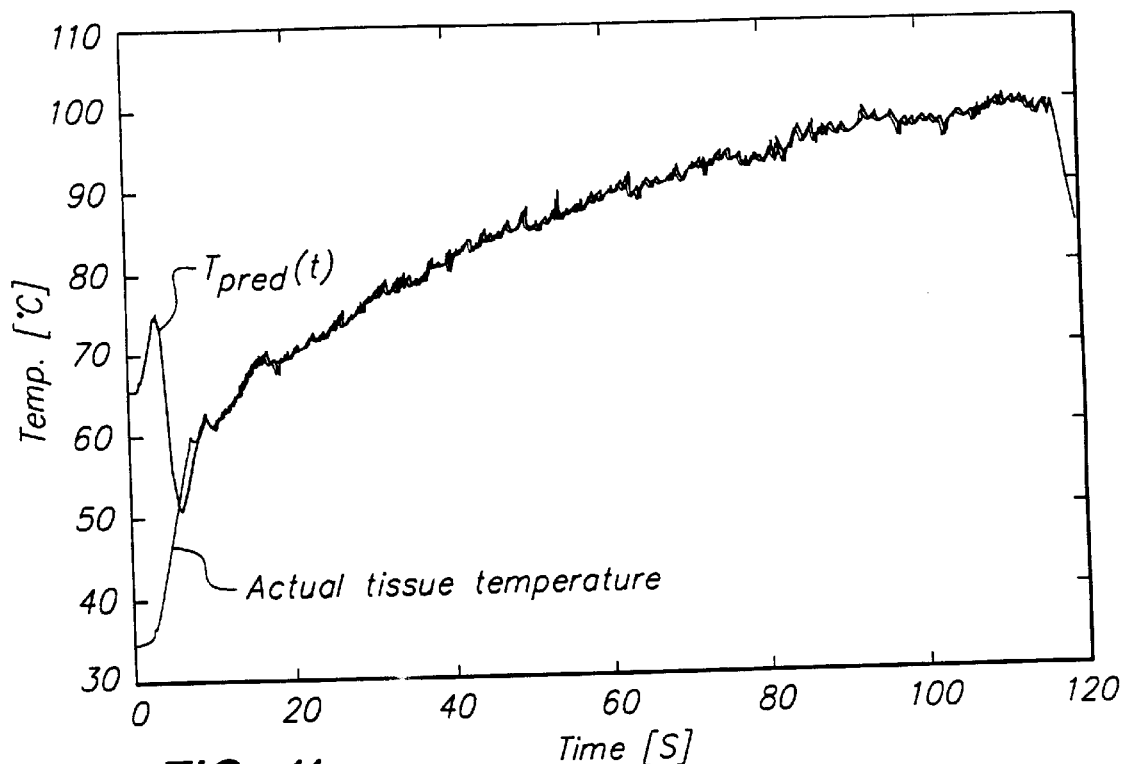
FIG. 11 is a graph presenting a comparison, for an electrode-tissue angle of 90°, of the temperature variations with time when the actual highest tissue temperature controlled the application of radio frequency energy compared when the predicted maximum tissue temperature output of the network shown in FIG. 10 was used as the control input.

FIG. 11 presents a comparison, for an electrode-tissue angle of 90°, of the temperature variations with time, at a constant power of 7 W, between actual and predicted maximal tissue temperature. The comparison was conducted after the training sessions and with data different than the data used for training, acquired using the apparatus shown in FIG. 6. The comparison shows good correspondence between the two control inputs, once overshoot and settling time converge to zero.

B. Prediction Based Upon Fuzzy Logic

Figure 12:
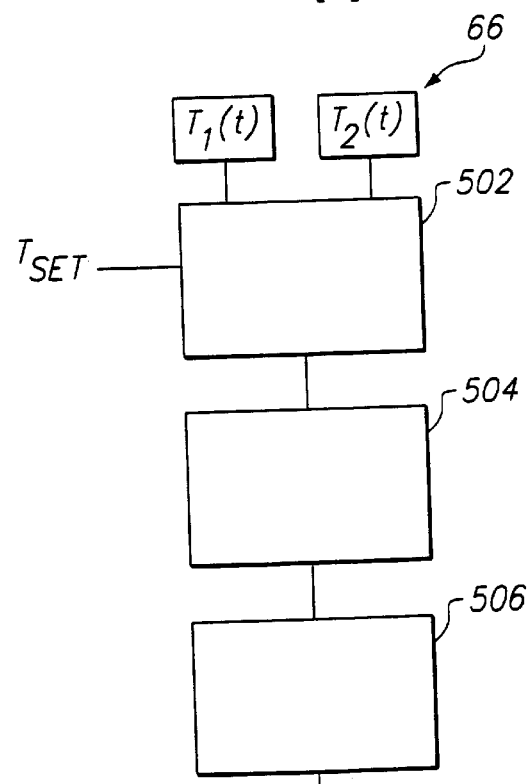
FIG. 12 is a schematic view of the implementation of fuzzy logic to predict maximum tissue temperature.

The dependence of maximum tissue temperature on $T_1$ and $T_2$ can also be approximated using fuzzy logic. FIG. 12 shows an alternative embodiment of the temperature processor 66 which derives $P_{DEMAND}$ using fuzzy logic control principles. In this implementation, the processor 66 includes a fuzzifier 502, which receives as inputs the temperature signals $T_1(t)$ and $T_2(t)$ from the sensing elements 30 and 32. The fuzzifier 502 also receives TST as input, either as a constant value or a value that changes over time. The fuzzifier 502 converts the pairs of $T_1(t)$ and $T_2(t)$ input data to fuzzy inputs based upon reference to $T_{SET}$ on a relative basis. For example, the fuzzy inputs can determine the degree (or membership function) to which a given pair of $T_1(t)$ and $T_2(t)$ is, compared to $T_{SET}$, "cool" or "warm" or "warmer" or "hot".

These fuzzy inputs are passed through an I/O mapper 504 which converts them to fuzzy outputs by translating the inputs into descriptive labels of power. This is accomplished, for example, by using linguistic "if. . . then" rules, like "if the fuzzy input is . . . then the fuzzy output is . . . ." Alternatively, more complex mapping matrical operators can be used.

For example, if the $T_{1/2}$pair is "cool," the I/O mapper 504 outputs the descriptive label "Largest Positive," to indicate that a large relative increase in power is required. By the same token, if the $T_{1/2}$pair is "hot," the I/O mapper 504 outputs the descriptive label "Largest Negative," to indicate that large relative decrease in power is required. The intermediate fuzzy inputs "warm" and "warmer" produce intermediate descriptive labels as fuzzy outputs, such as "Smallest Positive" and "Smallest Negative."

These fuzzy outputs are passed through a defuzzifier 506. The defuzzifier 506 also receives actual power P(t) as an input, since the fuzzy outputs refer to variations in P(t). Based upon P(t) and the variations required based upon the fuzzy outputs, the defuzzifier 506 derives $P_{DEMAND}(t)$.

To define proper reference sets and the rules of the I/O mapper 504, it may be required that the fuzzy logic controller be trained on a known set of data before use.

IV. Other Temperature sensing Embodiments

A. Multiple Electrodes

Figure 13:
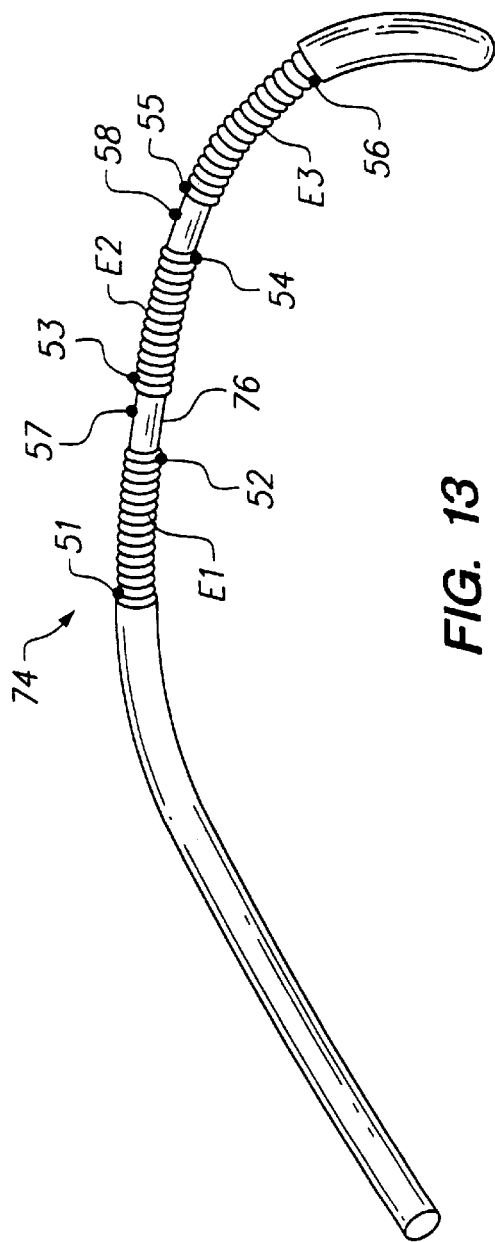
FIG. 13 is a flexible, multiple electrode element with multiple temperature sensing elements that can be used to predict maximum tissue temperature according to the invention.

FIG. 13 shows a flexible ablating element 74, which includes multiple, electrode elements, designated E1, E2, and E3 arranged in a spaced apart, segmented relationship along a flexible catheter body 76. The electrode elements can comprise generally rigid electrode rings, or spirally wound lengths of wire (as FIG. 13 shows), or electrode material coated upon the body 76.

As FIG. 13 shows, each electrode element E1, E2, and E3 carries at least one and, preferably, at least two, temperature sensing elements, designated S1 to S6. When the electrode elements exceed about 10 mm in length (as FIG. 13 contemplates), the temperature sensing elements S1 to S6 are preferably located at the edges of electrode elements E1 to E3, where the electrode elements abut the underlying, non-electrically-conductive catheter body 76. These sensing elements S1 to S6 are positioned to sense the temperature of the electrode elements.

The sensing elements S1 to S6 can be secured to the electrode elements in various ways. For example, they can be secured to the inside surface of the electrode elements, or sandwiched between the inside surface of the electrode and the underlying flexible body.

Alternatively, the sensing elements S1 to S6 can be threaded up through the windings in the electrode elements to lay upon its exterior surface.

Regardless of the particulars, the sensing elements S1 to S6 are electrically insulated from the electrode elements, such as, for example, being encapsulated in an epoxy or PTFE coating, as described before.

As FIG. 13 also shows, additional temperature sensing elements S7 and S8 are preferably located between adjacent electrode elements E1 to E3. These temperature sensing elements S7 and S8 are positioned to sense tissue temperature between the electrode elements.

In this arrangement, each sensing element S7 and S8 is threaded through the flexible body between adjacent electrode segments E1 to E3. When the sensing element 80 comprises a thermocouple, an epoxy material, such as Master Bond Polymer System EP32HT (Master Bond Inc., Hackensack, N.J.), encapsulates the thermocouple junction, while also securing it to the flexible body. Alternatively, the thermocouple junction can be coated in a thin layer of polytetrafluoroethylene (PTFE) material. When used in thicknesses of less than about 0.002 inch, these materials have the sufficient insulating properties to electrically insulate the thermocouple junction from the associated electrode segment E1 to E3. The use of such materials typically will not be necessary when thermistors are used, because conventional thermistors are already encapsulated in an electrically insulating and thermally conducting material.

Further details of such multiple electrode structures are disclosed in copending U.S. application Ser. No. 08/286,930, filed Aug. 8, 1994, entitled "Systems and Methods for Controlling Tissue Ablation Using Multiple Temperature Sensing Elements" and its continuation-in-part application Ser. No. 08/439,824, filed May 12, 1995, entitled "Systems and Methods for Controlling Tissue Ablation Using Multiple Temperature Sensing Elements."

In this embodiment, the temperature acquisition system 64 is coupled to all temperature sensing elements S1 to S8. The system 64 continuously samples at prescribed time periods, t, the analog signals generated by all the sensing elements S1 to S8 based upon locally sensed temperature conditions. The system 64 converts the separate analog signals of the sensing elements S1 to S8 into individual, proportional digital signals. The digital signals from sensing elements S7 and S8 located between adjacent electrode elements approximate inter-electrode tissue temperatures $T_{n,1}(t)$, where n identifies a particular one of the sensing elements S7 or S8. The digital signals from sensing elements S1 to S6 located on the electrode elements E1 to E3 correspond to electrode temperatures $T_{k,2}(t)$, where k identifies a particular one of the sensing elements S1 to S6.

In this embodiment, the temperature processing element 66 is coupled to the temperature acquisition system 64 to receive as input the digital signal temperatures $T_{n,1}(t)$ and electrode temperatures $T_{k,2}(t)$. The processing element 66 applies prescribed criteria to these actual temperature signals to derive, for the sampled time interval, a prediction of the hottest tissue temperature contacting each electrode element $T_{m,pred}(t)$, where m identifies a particular electrode element.

Figure 17:
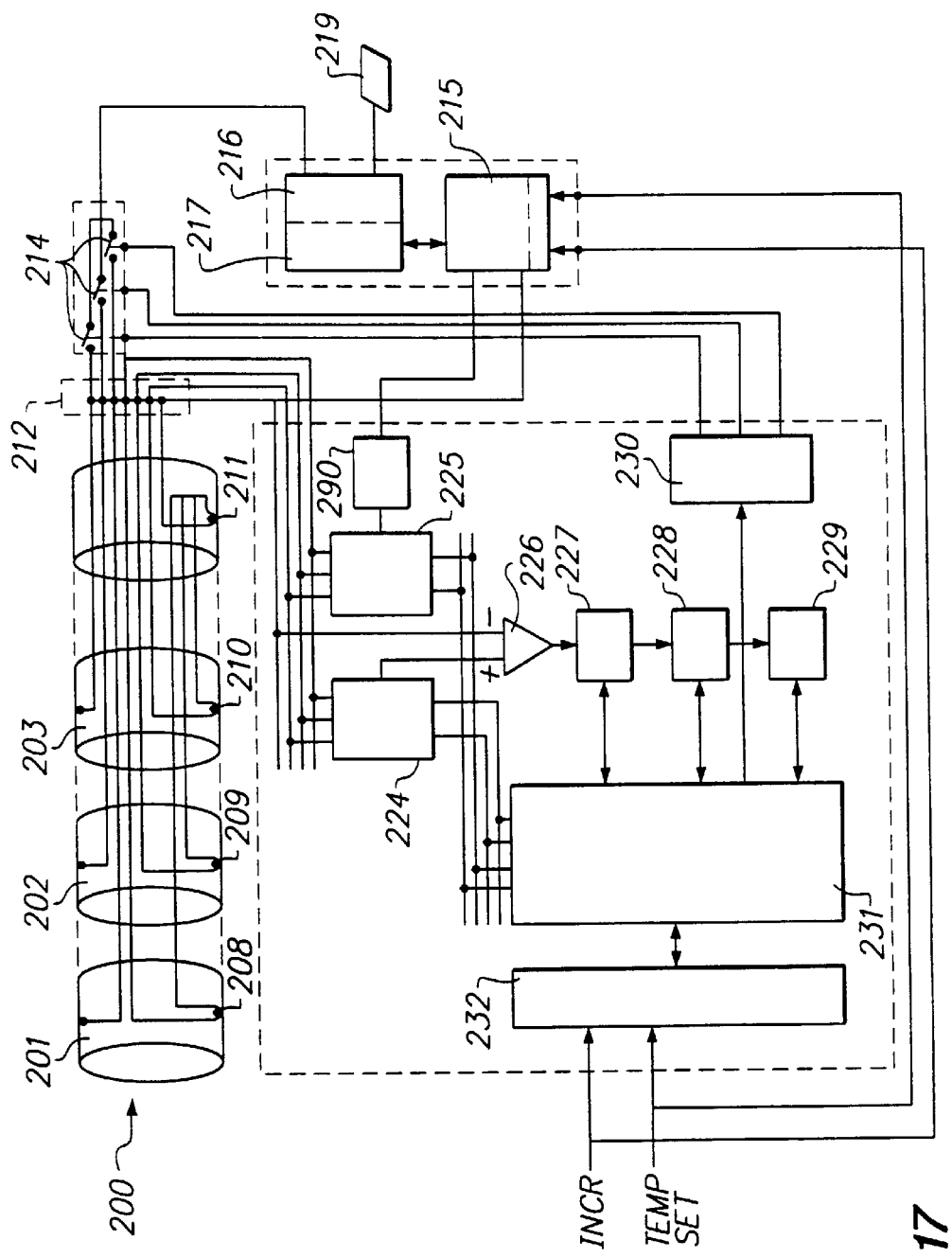

FIG. 17 shows, in schematic form, a representative system 200 for applying ablating energy by multiple electrodes based, at least in part, upon local temperature conditions sensed by multiple sensing elements.

In FIG. 17, the multiple sensing elements comprise thermocouples 208, 209, and 210 individually associated with multiple electrodes 201, 202, and 203. It should be appreciated that more thermocouples could also be associated with each electrode (as FIG. 13 shows), and/or thermocouples can be located between electrodes (as FIG. 13 also shows). The system 200 also includes a common reference thermocouple 211 carried within the coupler element 211 for exposure to the blood pool. The common reference thermocouple 211 could also be located externally, for example, in a catheter handle or in the generator, if maintained there at a known temperature. Alternatively, other kinds of temperature sensing elements can be used, like, for example, thermistors, fluoroptic sensors, and resistive temperature sensors, in which case the reference sensor 211 would typically not be required.

The system 200 further includes an indifferent electrode 219 for operation in a uni- polar mode.

The system 200 includes a source 217 of ablating energy. In FIG. 17, the source 217 generates radio frequency (RF) energy. The source 217 is connected (through a conventional isolated output stage 216) to an array of power switches 214, one for each electrode region 201, 202, and 203. A connector 212 (carried by the probe handle) electrically couples each electrode region 201, 203, 203 to its own power switch 214 and to other parts of the system 200.

The system 200 also includes a microcontroller 231 coupled via an interface 230 to each power switch 214. The microcontroller 231 turns a given power switch 214 on or off to deliver RF power from the source 217 individually to the electrode regions 201, 202, and 203. The delivered RF energy flows from the respective electrode region 201, 202, and 203, through tissue, to the indifferent electrode 219, which is connected to the return path of the isolated output stage 216.

Figure 18:
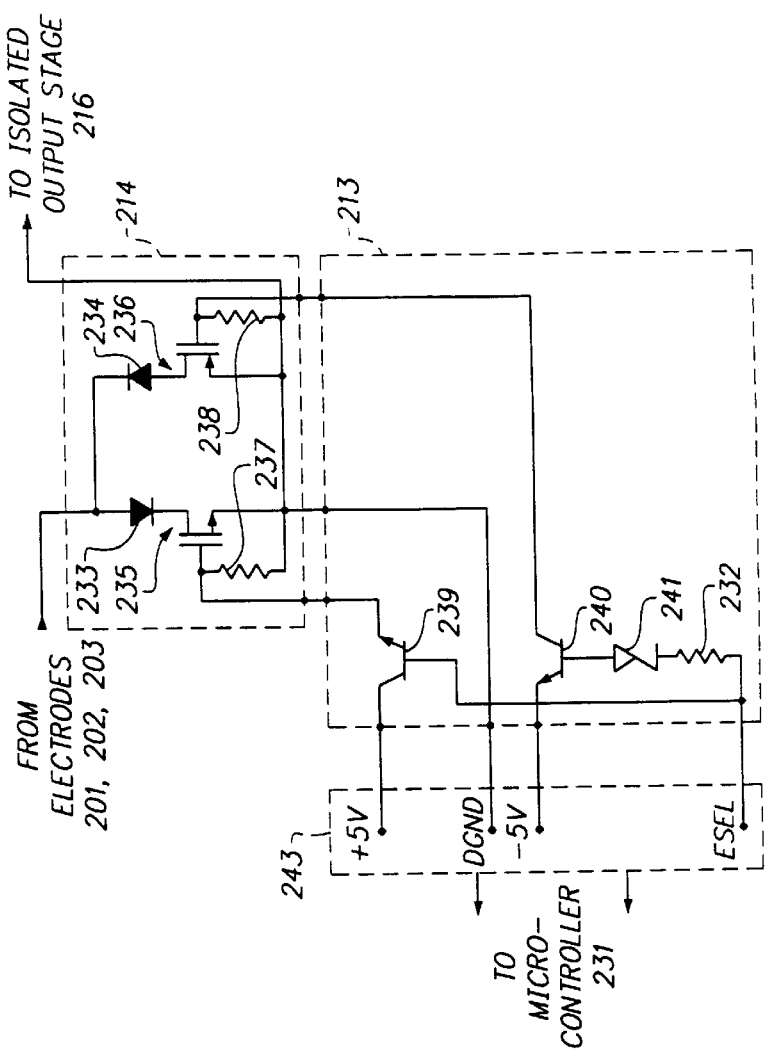
FIGS. 17 and 18 are schematic views of a system for controlling the application of ablation energy to multiple electrodes using multiple predicted maximum tissue temperature inputs.

The power switch 214 and interface 230 configuration can vary according to the type of ablating energy being applied. FIG. 18 shows a representative implementation for applying RF ablating energy.

In this implementation, each power switch 214 includes an N-MOS power.transistor 235 and a P-MOS power transistor 236 coupled in between the respective electrode region 201, 202, and 203 and the isolated output stage 216 of the power source 217.

A diode 233 conveys the positive phase of RF ablating energy to the electrode region. A diode 234 conveys the negative phase of the RF ablating energy to the electrode region. Resistors 237 and 238 bias the N-MOS and P-MOS power transistors 235 and 236 in conventional fashion.

The interface 230 for each power switch 214 includes two NPN transistors 239 and 240. The emitter of the NPN transistor 239 is coupled to the gate of the N-MOS power transistor 235. The collector of the NPN transistor 240 is coupled to the gate of the P-MOS power transistor 280.

The interface for each power switch 214 also includes a control bus 243 coupled to the microcontroller 231. The control bus 243 connects each power switch 214 to digital ground (DGND) of the microcontroller 231. The control bus 243 also includes a (+) power line (+5V) connected to the collector of the NPN transistor 239 and a (−) power line (−5V) connected to the emitter of the NPN interface transistor 240.

The control bus 243 for each power switch 214 further includes an $E_{SEL}$ line. The base of the NPN transistor 239 is coupled to the $E_{SEL}$ line of the control bus 243. The base of the NPN transistor 240 is also coupled the $E_{ESEL}$ line of the control bus 243 via the Zener diode 241 and a resistor 232. $E_{ESEL}$ line connects to the cathode of the Zener diode 241 through the resistor 232. The Zener diode 241 is selected so that the NPN transistor 240 turns on when $E_{ESEL}$ exceeds about 3 volts (which, for the particular embodiment shown, is logic 1).

It should be appreciated that the interface 230 can be designed to handle other logic level standards. In the particular embodiment, it is designed to handle conventional TTL (transistor transfer logic) levels.

The microcontroller 231 sets $E_{ESEL}$ of the control bus 243 either at logic 1 or at logic 0. At logic 1, the gate of the N-MOS transistor 235 is connected to (+) 5 volt line through the NPN transistors 239. Similarly, the gate of the P-MOS transistor 236 is connected to the (−) 5 volt line through the NPN transistor 240. This conditions the power transistors 235 and 236 to conduct RF voltage from the source 217 to the associated electrode region. The power switch 214 is "on".

When the microcontroller 231 sets $E_{ESEL}$ at logic 0, no current flows through the NPN transistors 239 and 240. This conditions the power transistors 235 and 236 to block the conduction of RF voltage to the associated electrode region. The power switch 214 is "off." The system 200 (see FIG. 17) further includes two analog multiplexers (MUX) 224 and 225. The multiplexers 224 and 225 receive voltage input from each thermocouple 208, 209, 210, and 211. The microcontroller 231 controls both multiplexers 224 and 225 to select voltage inputs from the multiple temperature sensing thermocouples 208, 209, 210, and 211.

The voltage inputs from the thermocouples 208, 209, 210, and 211 are sent to front end signal conditioning electronics. The inputs are amplified by differential amplifier 226, which reads the voltage differences between the copper wires of the thermocouples 208/209/210 and the reference thermocouple 211. The voltage differences are conditioned by element 227 and converted to digital codes by the analog-to-digital converter 228. The look-up table 229 converts the digital codes to temperature codes.

In one preferred implementation, the microcontroller 316 operates the power switch interface 230 to deliver RF power from the source 217 in multiple pulses of duty cycle 1/N, where N is the number of electrode segments.

With pulsed power delivery, the amount of power ($P_{E(J)}$) conveyed to each individual electrode region E(J) is expressed as follows:

$$P_{E(J)} \sim AMP_{E(J)}^2 \times DUTYCYCLE_{E(J)}$$

where:

$AMP_{E(J)}$ is the amplitude of the RF voltage conveyed to the electrode region E(J), and $DUTYCYCLE_{E(J)}$ is the duty cycle of the pulse, expressed as follows:

$$DUTYCYCLE_{E(J)} = \frac{TON_{E(J)}}{TON_{E(J)} + TOFF_{E(J)}}$$

where:

$TON_{E(J)}$ is the time that the electrode region E(J) emits energy during each pulse period, $TOFF_{E(J)}$ is the time that the electrode region E(J) does not emit energy during each pulse period.

The expression $TON_{E(J)} + TOFF_{E(J)}$ represents the period of the pulse for each electrode region E(J).

In this mode, the microcontroller 231 collectively establishes duty cycle ($DUTYCYCLE_{E(J)}$) of 1/N for each electrode region (N being equal to the number of electrode regions).

The microcontroller 231 may sequence successive power pulses to adjacent electrode regions so that the end of the duty cycle for the preceding pulse overlaps slightly with the beginning of the duty cycle for the next pulse. This overlap in pulse duty cycles assures that the source 217 applies power continuously, with no periods of interruption caused by open circuits during pulse switching between successive electrode regions.

In this mode, the microcontroller 231 cycles in successive data acquisition sample periods. During each sample period, the microcontroller 231 selects individual sensors S(J,K), and voltage differences are read by the predictor 290 (through MUX 225) and converted to temperature codes $T_{PRED}$, which are transmitted to the controller 215.

The predictor 290 receives the temperature codes. In the preferred implementation, when there are multiple temperature sensing elements on a given electrode element, the predictor selects as $T_{k,2}$ the hottest of the electrode temperatures sensed by the sensing elements on the electrode element. Also, when the electrode element is bounded by both side by a tissue temperature sensing element, the controller predictor also selects as $T_{n,1}$ the hottest of the tissue temperatures sensed by adjacent tissue sensing elements.

Using the selected values of $T_{n,1}$ (t) and $T_{k,2}$ (t), the predictor derives $T_{m,PRED}$ (t) in any of the manners above described for each electrode element.

In this mode, the controller 215 compares the predicted temperature $T_{PRED}$ for each electrode during each data acquisition period to a set point temperature $T_{SET}$. Based upon this comparison, the controller 215 varies the amplitude $AMP_{E(J)}$ of the RF voltage delivered to the electrode region, while the microcontroller 231 maintains the $DUTYCYCLE_{E(J)}$ for that electrode region and all other electrode regions, to establish and maintain $T_{PRED}$ at the set point temperature $T_{SET}$.

The manner in which the controller 215 governs $AMP_{E(J)}$ can incorporate proportional control methods, proportional integral derivative (PID) control methods, or fuzzy logic control methods.

B. Self-Heated Temperature Sensing Element

Figure 14:
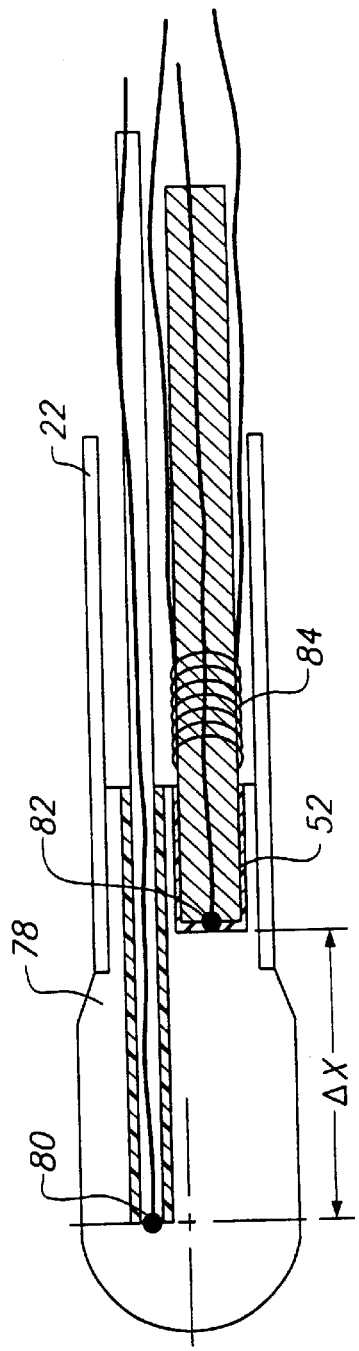
FIG. 14 is an electrode with multiple temperature sensing elements, and a heating element to heat the electrode, which can be used to predict maximum tissue temperature according to the invention.

FIG. 14 shows another alternative embodiment of an electrode 78 with multiple temperature sensing elements 80 and 82. In FIG. 14, both temperature sensing elements 80 and 82 are connected by soldering or by thermally conducting adhesive to the thermal mass of the electrode 78.

Figure 15:
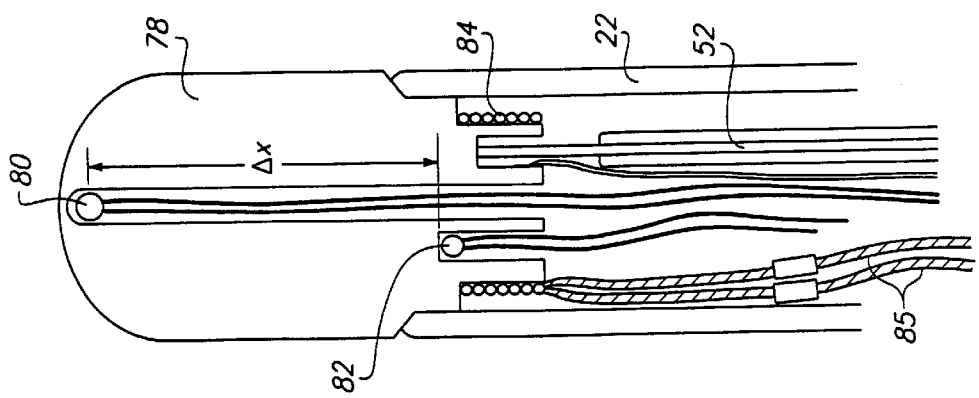
FIG. 15 is an alternative embodiment of an electrode with multiple temperature sensing elements and a heating element which can be used to predict maximum tissue temperature according to the invention.

Alternatively (as FIG. 15 shows), the sensing element 80 can be located to sense tissue temperature, as sensing element 30 in FIG. 4.

In addition a resistance heating element 84 is provided for the purpose of heating the thermal mass of the electrode 78. In the illustrated embodiment shown in FIG. 14, the heating element 84 extends in intimate contact about the metal steering spring 52. As the heating spring 52 heats up, the heat is conducted to the thermal mass of the electrode 78.

Alternatively (as FIG. 15 shows), the heating element 84 can be wrapped about a portion of the electrode 78 under the catheter body 22. In either embodiment, the heating element 84 is located in good thermal conductive contact with the electrode for ohmic heating of the element 84 with DC energy to thereby heat the electrode 78 by conductive heat transfer.

The heating element 84 can comprise an insulated constantan wire having a high resistance, or Nichrome or insulated toaster wire having the same characteristic. As FIG. 15 shows, the heating wire 84 is mated with low resistance copper wire 85 close to the electrode 78. The copper wire 85 extends the rest of the way through the catheter body 22.

The distance (Δx in FIG. 15) between the two sensing elements 80 and 82 should preferably be maximized to the fullest extent possible, given the size of the electrode 78. For example, for an 8F/4 mm electrode, Δx should be at least 3 mm.

Figure 16:
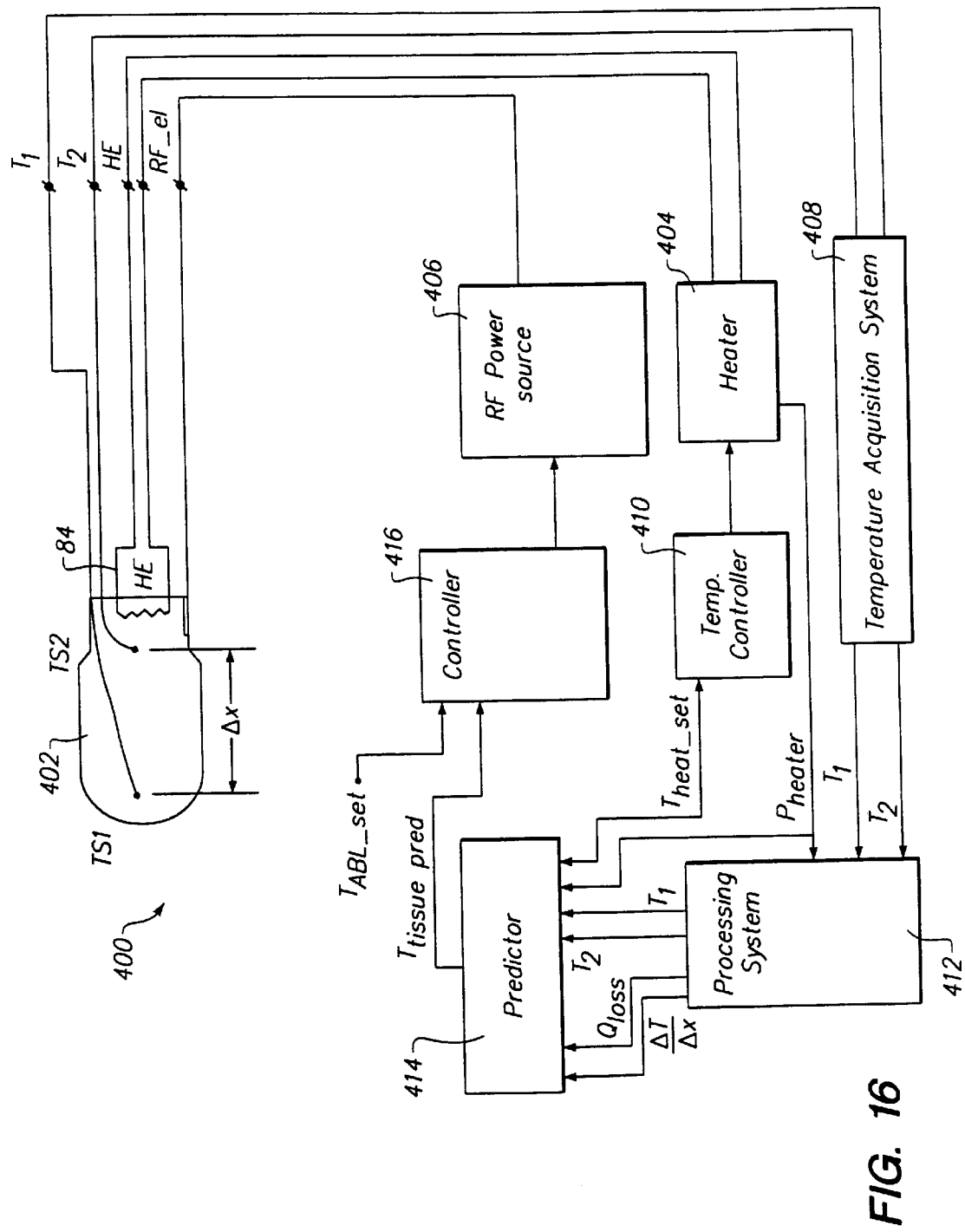
FIG. 16 is a system including an electrode like that shown in either FIG. 14 or FIG. 15, which can be used to predict maximum tissue temperature according to the invention.

FIG. 16 shows a system 400 including an electrode 402 having two temperature sensors $TS_1$ and $TS_2$. The electrode 402 also includes the heating element HE 84 heated by the heater 404. The electrode 402 is coupled to the RF power source 406.

The temperatures read by $TS_1$ and $TS_2$ ($T_1$ and $T_2$) are acquired by the temperature acquisition system 408. The system 400 operates in two phases.

During this first phase, no ablating energy is directly applied to the electrode 402. HE is actuated by the heater 404 so that $T_2$ is kept about a set value $T_{heat\_set}$. The temperature controller 410 which controls the heater 404 can use appropriate control techniques, such as PID, etc.

During this phase, the temperatures $T_1$ and $T_2$ are acquired by the acquisition system 408. The electrical power generated by the heater 404 is also measured, $P_{heater}$.

$T_1$, $T_2$ and $P_{heater}$ are inputted to a processing system 412, which, based upon the distance Δx between temperature sensing elements $TS_1$ and $TS_2$ and the whether $TS_1$ is sensing electrode or tissue temperature, computes the heat loss, $Q_{loss}$, and the temperature spatial gradient ΔT/Δx. The processing system 412 can acquire information concerning the electrode configuration from the physician, or by a read-only-memory chip and the equivalent associated with the electrode which the processing system 412 can interrogate. The heat loss, $Q_{loss}$, will depend on the thermal conductivity, density and heat capacity of the metal of the electrode 402, the amount of electrical and thermal contact between tissue and electrode, and the convective cooling induced by the blood flow. Therefore, $Q_{loss}$ and ΔT/Δx are indications of the present status of the electrical-thermal system at the tissue-electrode-blood interface. This status information is later used to predict and control the tissue temperature during ablation in the second phase.

In the second phase, ablation energy is applied to tissue through the electrode 402. The values of $T_1$, $T_2$, $Q_{loss}$, ΔT/Δx, Theat set , and $P_{heater}$ are fed as inputs to a predictor 414.

The predictor 414 includes in look-up table form relationships among $T_1$, $T_2$, $Q_{loss}$, ΔT/Δxp $T_{heat\_set}$, $P_{heater}$, and $T_{PRED}$. The inputs to the table are $T_1$, $T_2$, $Q_{loss}$, ΔT/Δx, $T_{heat\_set}$, $P_{heater}$, and the output of the table is $T_{PRED}$. The look-up table is constructed based on experimental data acquired with an apparatus similar to that shown in FIG. 6, using an electrode like that shown in FIGS. 14 and 15. The table correlates experimentally measured $T_1$, $T_2$ $Q_{loss}$, ΔT/Δx, $T_{heat\_}^{set}$, $P_{heater}$ to experimentally measured maximum tissue temperature. The output $T_{PRED}$ of the look-up table is best-fitted to the experimental data.

The values of $Q_{loss}$, ΔT/Δx, $T_{heat\_set}$, $P_{heater}$ taken during the first phase in connection with $T_1$ and $T_2$ characterize the system for input to the table. The current status of $T_1$ and $T_2$ taken during the second phase provide from the table a unique output predicting the maximal tissue temperature.

The predictor 414 outputs the predicted tissue temperature $T_{PRED}$. $T_{PRED}$ and a set temperature value $T_{ABL\_set}$ are fed as inputs to a controller 416, which controls the RF power source 406. The controller 416 controls predicted tissue temperature about $T_{ABL\_set}$.

The illustrated and preferred embodiments envision the use of micro-processor controlled components using digital processing to analyze information and generate feedback signals. It should be appreciated that other logic control circuits using micro-switches, AND/OR gates, invertors, and the like are equivalent to the micro-processor controlled components and techniques shown in the preferred embodiments. It should also be appreciated that the algorithms disclosed in this Specification lend themselves to implementation using either digital or analog devices.

Various features of the invention are set forth in the claims that follow.

We claim:

1. An apparatus for heating body tissue comprising:
an electrode to transmit heating energy into a body tissue region;
a first sensing element coupled to the electrode for measuring a first temperature;
a second sensing element coupled to the electrode for measuring a second temperature; and
a processing element coupled to the first and second sensing elements to process the first and second temperatures and to derive therefrom a prediction of maximum temperature of the body tissue region.

2. An apparatus according to claim 1
wherein the electrode is configured to transmit radio frequency energy.

3. An apparatus according to claim 1
wherein the processing element includes a neural network predictor.

4. An apparatus according to claim 1
wherein the processing element derives the maximum body tissue temperature prediction based, at least in part, upon fuzzy logic.

5. An apparatus according to claim 1
wherein the processing element processes changes in the first and second temperatures over time to derive the maximum tissue temperature prediction.

6. An apparatus according to claim 1
wherein the processing element derives the maximum body tissue temperature prediction based, at least in part, upon the first temperature measured by the first sensing element and the second temperature measured by the second sensing element.

7. An apparatus according to claim 1
wherein the electrode carries at least one of the first and second sensing elements.

8. An apparatus according to claim 1
wherein at least one of the senising elements is in thermal conductive contact with the electrode.

9. An apparatus according to claim 1
and further including a second electrode spaced along a body from the first mentioned electrode, and
wherein at least one of the sensing elements is located on the body between the first and second electrodes.

10. An apparatus according to claim 1
and further including a third temperature sensing element associated with the second electrode to measure a third temperature, and
wherein the processing element derives a maximum tissue temperature prediction from the first, second and third temperatures.

11. An apparatus according to claim 1 wherein
the processing element employs the prediction of maximum temperature of the body tissue region to control the transmission of heating energy by the electrode based, at least in part, upon the prediction of maximum temperature of the bode tissue region.

12. An apparatus according to claim 11 wherein
the processing element controls the transmission of heating energy by the electrode based upon comparing the prediction of the maximum temperature of the body tissue region to a prescribed temperature.

13. An apparatus according to claim 12 wherein
the prescribed temperature remains essentially constant over time.

14. An apparatus according to claim 12 wherein
the prescribed temperature changes at least once as a function of time.

15. An apparatus according to claim 1 wherein
the processing element generates an output based upon the prediction of maximum temperature of the body tissue region.

16. An apparatus according to claim 15 wherein
the apparatus further includes means for inputting a prescribed temperature and wherein the processing element generates the output based upon comparing the prediction of maximum temperature of the body tissue region with the prescribed temperature.

17. An apparatus according to claim 16, wherein
the prescribed temperature remains essentially constant over time.

18. An apparatus according to claim 16, wherein
the prescribed temperature changes at least once as a function of time.

19. An apparatus according to claim 16 wherein
the processing element applies control principles to compare the prediction of maximum temperature of the body tissue region to the prescribed temperature to generate the output, whereby the control principles are selected from the group consisting of proportional control principles, proportional integral derivative (PID) control principles, adaptive control principles, neural network control principles and fuzzy logic control principles.

20. An apparatus for ablating body tissue comprising
an electrode for contacting a body tissue region to transmit ablation energy into the body tissue region,
a first sensing element in thermal communication with the electrode for measuring temperature of the electrode,
a second sensing element carried by the electrode for measuring temperature of body tissue contacting the electrode, and
a processing element coupled to the first and second sensing elements to process the first and second temperatures and to derive therefrom a prediction of maximum temperature of the body tissue region.

21. An apparatus according to claim 20 wherein the electrode transmits radio frequency energy.

22. An apparatus according to claim 20 wherein the processing element includes a neural network predictor.

23. An apparatus according to claim 20
wherein the processing element derives the maximum body tissue temperature prediction based, at least in part, upon fuzzy logic.

24. An apparatus according to claim 20
wherein the processing element processes changes in the first and second temperatures over time to derive the maximum tissue temperature prediction.

25. An apparatus according to claim 20
wherein the processing element derives the maximum body tissue temperature prediction based, at least in part, upon a first temperature measured by the first sensing element and a second temperature measured by the second sensing element.

26. An apparatus according to claim 20 wherein the electrode carries at least one of the first and second sensing elements.

27. An apparatus according to claim 20 wherein the processing element controls the transmission of ablation energy by the electrode based, at least in part, upon the maximum body tissue temperature prediction.

28. An apparatus according to claim 27 wherein the apparatus further includes means for inputting a prescribed temperature and wherein the processing element controls the transmission of ablation energy based upon comparing the maximum body tissue temperature prediction to the prescribed temperature.

29. An apparatus according to claim 20 and further including, a second electrode spaced along a body from the first mentioned electrode, and wherein the second sensing element is located on the body between the first and second electrodes.

30. An apparatus according to claim 29 and further including a third temperature sensing element to measure temperature of the second electrode.

31. An apparatus according to claim 20 wherein the processing element generates an output based upon the maximum body tissue temperature prediction.

32. An apparatus according to claim 31 wherein the processing element generates the output based upon comparing the maximum body tissue temperature prediction to a prescribed temperature.

33. An apparatus according to claim 32 wherein the prescribed temperature remains essentially constant over time.

34. An apparatus according to claim 32 wherein the prescribed temperature changes at least once as a function of time.

35. A system for transmitting energy to an electrode for heating body tissue comprising
a generator coupled to an electrode to supply energy to the electrode for heating a body tissue region,
a controller coupled to the generator to control the generator's supply of energy to the electrode, the controller comprising
a first sensing element coupled to the electrode for measuring a first temperature,
a second sensing element coupled to the electrode for measuring a second temperature, and
a processing element coupled to the first and second sensing elements to process the first and second temperatures and to derive therefrom a prediction of maximum temperature of the body tissue region and for generating a signal to control energy supplied by the generator based, at least in part, upon the maximum body tissue temperature prediction.

36. A system according to claim 35 and further including a second electrode spaced along a body from the first mentioned electrode, and wherein at least one of the sensing elements is located on the body between the first and second electrodes.

37. A system according to claim 35 wherein the processing elements derives the maximum body tissue temperature prediction based, at least in part, upon a first temperature measured by the first sensing element and a second temperature measured by the second sensing element.

38. A system according to claim 35 wherein at least one of the sensing elements is in thermal conductive contact with the electrode.

39. A system according to claim 38 and further including a third temperature sensing element associated with the second electrode to measure a third temperature, and wherein the processing element derives the maximum tissue temperature prediction from the first, second and third temperatures temperatures.

40. A system according to claim 35 wherein the processing element controls the transmission of heating energy by the electrode based, at least in part, upon the maximum body tissue temperature prediction.

41. A system according to claim 40 wherein the apparatus further includes means for inputting a prescribed temperature and wherein the processing element controls the transmission of heating energy based upon comparing the maximum body tissue temperature prediction to the prescribed temperature.

42. A system according to claim 41 wherein the prescribed temperature remains essentially constant over time.

43. A system according to claim 41 wherein the prescribed temperature, changes at least once as a function of time.

44. A system for supplying energy to an electrode for ablating body tissue comprising
a generator adapted to be coupled to an electrode to supply energy to the electrode for ablating body tissue within a region,
a controller coupled to the generator to control the generator's supply of energy to the electrode, the controller comprising
a first sensing element in thermal communication with the electrode for measuring temperature of the electrode,
a second sensing element carried by the electrode for measuring temperature of body tissue contacting the electrode, and
a processing element coupled to the first and second sensing elements to process the first and second temperatures and to derive therefrom a prediction of maximum temperature of the body tissue region and for generating a signal to control energy supplied to the generator based, at least in part, upon the maximum body tissue temperature prediction.

45. A system according to claim 44 wherein the processing element controls the transmission of ablation energy by the electrode based, at least in part, upon the maximum body tissue temperature prediction.

46. A system according, to claim 44 wherein the electrode carries at least one of the first and second sensing elements.

47. A system according to claim 44 and further including, a second electrode spaced alone a body from the first mentioned electrode, and wherein the second sensing element is located on the body between the first and second electrodes.

48. A system according to claim 47 and further including a third temperature sensing element to measure temperature of the second electrode.

49. A system according to claim 44 wherein the apparatus further includes means for inputting a prescribed temperature and wherein the processing element controls the transmission of ablation energy based upon comparing the maximum body tissue temperature prediction to the prescribed temperature.

50. A system according to claim 49 wherein the prescribed temperature remains essentially constant over time.

51. A system according to claim 49 wherein the prescribed temperature changes at least once as a function of time.

52. A method for heating body tissue comprising:

positioning an electrode to transmit heat energy to a body tissue region, applying energy to the electrode to heat the body tissue region, measuring a first temperature using a temperature sensing element associated with the electrode, measuring a second temperature using a temperature sensing element associated with the electrode, and processing the first and second temperatures to derive a prediction of maximum temperature of the body tissue region.

53. A method according to claim 52 and further including generating an output based upon the maximum body tissue temperature prediction.

54. A method according to claim 53 wherein the apparatus further includes means for inputting a prescribed temperature and wherein the output is based upon comparing the maximum body tissue temperature prediction to the prescribed temperature.

55. A method according to claim 54 wherein the prescribed temperature remains essentially constant over time.

56. A method according to claim 54 wherein the prescribed temperature changes at least once as a function of time.

* * * * *